United States Patent [19]

Pissiotas et al.

[11] 4,364,769
[45] Dec. 21, 1982

[54] 1,3,4-THIADIAZOLYLOXYPHENYLUREAS

[75] Inventors: Georg Pissiotas, Lörrach, Fed. Rep. of Germany; Otto Rohr, Therwil; Haukur Kristinsson, Bottmingen, both of Switzerland

[73] Assignee: Ciba-Geigy Corporation, Ardsley, N.Y.

[21] Appl. No.: 166,679

[22] Filed: Jul. 7, 1980

[30] Foreign Application Priority Data

Jul. 13, 1979 [CH] Switzerland ............... 6554/79

[51] Int. Cl.³ .............. A01N 47/28; A01N 47/30; C07D 285/12
[52] U.S. Cl. ................................ 71/90; 71/76; 548/136; 548/142
[58] Field of Search ........... 548/136, 142; 71/90, 71/76

[56] References Cited

FOREIGN PATENT DOCUMENTS 2101938 7/1971 Fed. Rep. of Germany ...... 548/144

OTHER PUBLICATIONS

Sandstrom, Advances in Heterocyclic Chemistry, vol. 9, (Academic Press, 1968), pp. 170–172.

*Primary Examiner*—Alton D. Rollins
*Attorney, Agent, or Firm*—Frederick H. Rabin

[57] ABSTRACT

The invention relates to novel 1,3,4-thiadiazolyloxyphenylureas which possess herbicidal properties and which have good selectivity in different crops of cultivated plants. The novel phenylureas have the general formula I

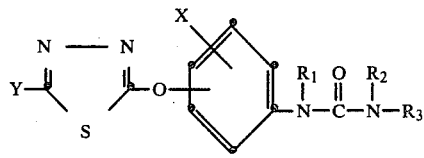

wherein
X is hydrogen, halogen or trifluoromethyl,
Y is hydrogen, $C_1$–$C_6$ alkyl which can be interrupted by oxygen or substituted by halogen or cyano; $C_3$–$C_6$ cycloalkyl, cyclopropylmethyl, phenyl which is unsubstituted or substituted by chlorine or $C_1$–$C_4$ alkyl; or is $C_1$–$C_4$ alkylthio, $C_1$–$C_4$ alkoxy, $C_1$–$C_4$ alkylsulfinyl or $C_1$–$C_4$ alkylsulfonyl, or a sulfamoyl group —$SO_2NR_2R_3$,
$R_1$ is hydrogen or $C_1$–$C_4$ alkyl,
$R_2$ is hydrogen, $C_1$–$C_6$ alkyl which can be interrupted by oxygen or substituted by halogen or cyano, or is $C_3$–$C_6$ alkenyl or $C_3$–$C_6$ alkynyl, or $C_3$–$C_6$ cycloalkyl, has the same meaning as $R_2$ or is $C_1$–$C_6$ alkoxy, or
$R_2$ and $R_3$, together with the nitrogen atom to which they are attached, can also form a 5- or 6-membered heterocyclic ring system which can contain an additional oxygen or sulfur atom or an imino group which is unsubstituted or substituted by $C_1$–$C_3$ alkyl.

22 Claims, No Drawings

1,3,4-THIADIAZOLYLOXYPHENYLUREAS

The present invention relates to novel 1,3,4-thiadiazolyloxyphenylureas which possess herbicidal properties, processes for their production, compositions which contain them, and their use for selectively controlling weeds in different crops of cultivated plants, e.g. cereals, maize, rice, cotton, sugar beet and soybeans.

Herbicidally active phenylureas have long been known and employed in the art. Their widespread use has made it possible on the one hand substantially to eliminate weeds from crops of cultivated plants such as cereals, but, on the other hand, has resulted in a proliferation of weeds which are more resistant to such herbicides.

Accordingly, it is the object of the present invention to provide phenylureas which, on the one hand, will control weeds which are still so far resistant, and which, on the other, are able to protect crops of cultivated crops, e.g. soybeans, which are not sufficiently resistant to the phytotoxicity of most known herbicides.

The novel 1,3,4-thiadiazolyloxyphenylureas have the formula I

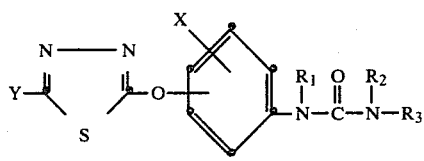

wherein

X is hydrogen, halogen or trifluoromethyl,

Y is hydrogen, $C_1$–$C_6$alkyl which can be interrupted by oxygen or substituted by halogen or cyano; $C_3$–$C_6$cycloalkyl, cyclopropylmethyl, phenyl which is unsubstituted or substituted by chlorine or $C_1$–$C_4$alkyl; or is $C_1$–$C_4$alkylthio, $C_1$–$C_4$alkoxy, $C_1$–$C_4$alkylsulfinyl or $C_1$–$C_4$alkylsulfonyl, or a sulfamoyl group —$SO_2NR_2R_3$, $R_1$ is hydrogen or $C_1$–$C_4$alkyl, $R_2$ is hydrogen, $C_1$–$C_6$alkyl which can be interrupted by oxygen or substituted by halogen or cyano, or is $C_3$–$C_6$alkenyl or $C_3$–$C_6$alkynyl, or $C_3$–$C_6$cycloalkyl, $R_3$ has the same meaning as $R_2$ or is $C_1$–$C_6$alkoxy, or $R_2$ and $R_3$, together with the nitrogen atom to which they are attached, can also form a 5- or 6-membered heterocyclic ring system which can contain an additional oxygen or sulfur atom or an imino group which is unsubstituted or substituted by $C_1$–$C_3$alkyl.

The alkyl radicals defined for Y, $R_1$, $R_2$ and $R_3$ can be both straight-chain and branched. Suitable radicals Y are in particular: hydrogen, methyl, ethyl, n-propyl, isopropyl, n-butyl, sec-butyl, isobutyl, tert-butyl, amyl, isoamyl, neopentyl, n-hexyl, and also hex-2-yl, methoxymethyl, methoxyethyl, cyanomethyl, cyanoethyl, 2-cyanopropyl, trifluoromethyl, trichloromethyl, cyclopropyl, cyclopropylmethyl, cyclobutyl, cyclopentyl, cyclohexyl, methylthio, alkylthio, n-propylthio, isopropylthio, n-butylthio, isobutylthio, sec-butylthio, tert-butylthio, methylsulfinyl, ethylsulfinyl, n-propylsulfinyl, isopropylsulfinyl, n-butylsulfinyl, isobutylsulfinyl, sec-butylsulfinyl, tert-butylsulfinyl, methylsulfonyl, ethylsulfonyl, n-propylsulfonyl, isopropylsulfonyl, n-butylsulfonyl, isobutylsulfonyl, sec-butylsulfonyl, tert-butylsulfonyl, as well as dimethylsulfamoyl and diethylsulfamoyl. The preferred identity of $R_1$ is hydrogen or methyl, and the preferred identities of $R_2$ and $R_3$ are methyl and methoxy.

The compounds of the formula I possess in general pronounced selective herbicidal properties and are especially useful for controlling weeds in crops of cultivated plants, particularly in crops of soybeans, cotton, cereals, maize and sugar beet.

When employed in a sufficiently high concentration, the compounds of the invention also act as total herbicides. Application can be both pre- and post-emergence, in which connection the rates of application can vary within wide limits, e.g. between 0.1 and 10 kg of active ingredient per hectare, but with the preferred range being between 0.5 and 5 kg of active ingredient per hectare.

The best action has been obtained with compounds of the following structural formulae:

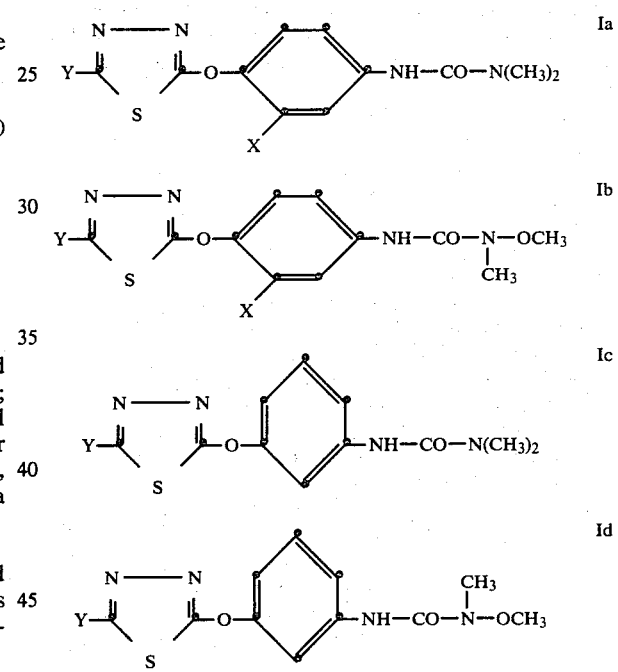

In the above formulae, X and Y have the given meanings. Particularly effective compounds are those in which Y is the trifluoromethyl, isopropyl, isobutyl, sec-butyl, tert-butyl, isoamyl, cyclopropyl, cyclopropylmethyl, methoxymethyl, 1-cyanopropyl, methylsulfonyl, isopropylsulfonyl or dimethylsulfamoyl group, as well as those in which X is the trifluoromethyl group and Y is the tert-butyl group.

In addition to containing the active ingredients of the formula I, the compositions of this invention contain a suitable carrier and/or other adjuvants. Suitable carriers and adjuvants can be solid or liquid and correspond to the substances customarily employed in the art of formulation, e.g. natural or regenerated mineral substances, solvents, diluents, dispersants, emulsifiers, wetting agents, tackifiers, thickeners, binders and/or fertilisers.

For use in herbicidal compositions, the compounds of the formula I can be processed to dusts, emulsifiable concentrates, granules, dispersions or as solutions or suspensions in conventional formulation.

The compounds of the formula I decompose in the soil after a relatively short time to form decomposition products which are rich in nitrogen and beneficial to plant nutrition.

To broaden the activity spectrum or to obtain a desired synergistic or also antagonistic effect it is also possible to employ these compounds together with known herbicides, pesticides or fungicides. Herbicides with which the compounds of the invention may be combined are e.g. one or more of a phenoxyaliphatic acid, a substituted urea, a triazine, a phenol, a nitrile, a bipyridilium compound, a substituted benzoic acid, a halogenated aliphatic acid, a carbamate, a thiocarbamate, a chloroacetamide, a diazine, a benzofuran, or an arsenic herbicide.

The phenoxyaliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or they may be of only slight herbicidal activity. Examples of the substituted phenoxyaliphatic acids which may be mentioned include 2,4-dichlorophenoxyacetic acid, 2-(2,4-dichlorophenoxy)propionic acid, 2-methyl-4-chlorophenoxyacetic acid, 2,4,5-trichlorophenoxyacetic acid, gamma-2,4-dichlorophenoxybutyric acid, gamma-2-methyl-4-chloro-phenoxybutyric acid, alpha-2-methyl-4-chlorophenoxypropionic acid, 2-(4-[2,4-dichlorophenoxy]phenoxy)propionic acid and 2-(4-[4-chlorophenoxy]phenoxy)propionic acid.

The substituted urea generally comprises a tri- or tetra-substituted urea such as N'-(3-chloro-4-methoxyphenyl)-N,N-dimethylurea, N'-(3-chloro-4-methylphenyl)-N,N-dimethylurea, N'-parachlorophenyl-N,N-dimethylurea, N-butyl-N'-(3,4-dichlorophenyl)-N-methylurea, N'-parachlorophenyl-O,N,N-trimethylisourea, N'-p-chlorophenyl-N-methoxy-N-methylurea, N,N-dimethyl-N'-phenylurea, 3-(4-bromophenyl)-1-methoxy-1-methylurea, 1-(2-benzothiazolyl)-3-methylurea, N,N-dimethyl-N'-(4-[1-methylethyl]-phenyl)urea, N'-(3,4-dichlorophenyl)-N-methoxy-N-methylurea, N,N-dimethyl-N'-[3-(trifluoromethyl)-phenyl]urea, N'-(3,4-dichlorophenyl)-N,N-dimethylurea or N'-(3-(1,1,2,2-tetrafluoroethoxy)-phenyl)N,N-dimethylurea.

The triazine herbicide generally comprises 2-chloro-4-(1-cyano-1-methylamino)-6-ethylamino-1,3,5-triazine or 2-isopropylamino-4-(3-methoxypropylamino)-6-methylthio-1,3,5-triazine or a compound of the formula:

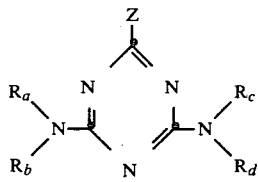

where Z is a halogen atom, an alkoxy group or alkylthio group, $R_a$ and $R_c$ are the same or different and are hydrogen or alkyl and $R_b$ and $R_d$ are the same or different alkyl groups, such as 2-chloro-4,6-bisethylamino-1,3,5-triazine, 2-chloro-4-ethylamino-6-diethylamino-1,3,5-triazine, 2-chloro-6-ethylamino-4-isopropylamino-1,3,5-triazine or 2,4-bis(isopropylamino)-6-methylthio-1,3,5-triazine.

The phenol herbicide generally comprises 4,6-dinitro-o-cresol, 4,6-dinitro-2-sec-butylphenol or pentachlorophenol. The nitrile herbicide generally comprises 3,5-diiodo-4-hydroxy-benzonitrile, 3,5-dibromo-4-hydroxybenzonitrile or 2,6-dichlorobenzonitrile. The bipyridilium herbicide generally comprises 1,1'-dimethyl-4,4'-bipyridylium dichloride or 1,1'-ethylene-2,2'-bipyridylium dibromide. The substituted benzoic acid herbicide generally comprises 2,3,6-trichlorobenzoic acid, 2-methoxy-3,6-dichlorobenzoic acid or N-(1,1-dimethylpropynyl)-3,5-dichlorobenzamide. The halogenated aliphatic acid herbicide generally comprises trichloroacetic acid or 2,2-dichloropropionic acid. The carbamate herbicide generally comprises isopropyl N-(3-chlorophenyl)carbamate, 4-chloro-2-butynyl N-(3-chlorophenyl)carbamate, methyl 3-(m-tolylcarbamoyloxy)phenylcarbamate, isopropyl N-(3-(N-ethyl-N-phenylcarbamoyloxy)phenyl)carbamate, or D-N-ethyl-2-(phenylcarbamoyloxy)propionamide. The thiocarbamate herbicide generally comprises S-ethyl N,N-dipropylthiocarbamate, S-ethyl N,N-diisobutylthiocarbamate, S-(2,3-dichloroallyl) N,N-diisopropylthiocarbamate, S-ethyl N-ethyl-N-cyclohexylthiocarbamate, S-propyl butylethylthiocarbamate or S-(2,3,3,-trichloroallyl) N,N-diisopropylthiocarbamate. The chloroacetamide herbicide generally comprises N,N-diallyl-2-chloroacetamide, N-isopropyl-2-chloroacetanilide, N-chloroacetyl-N-(2,6-diethylphenyl)glycine ethyl ester, N-(2,6-diethylphenyl)-N-(methoxymethyl)-2-chloroacetamide, N-(2-ethyl-6-methylphenyl)-N-(2-methoxy-1-methylethyl)-2-chloroacetamide, or N-chloroacetyl-N-(2-methyl-6-ethylphenyl)glycine isopropyl ester. The diazine herbicide generally comprises 5-bromo-6-methyl-3-sec-butyluracil, 3-cyclohexyl-5,6-trimethyleneuracil, 5-amino-4-chloro-2-phenyl-3-pyridazinone or 1,2-dihydropyridazine-3,6-dione. The benzofuran herbicide may be, for example, ethofumesate or 2,3-dihydro-3,3-dimethyl-benzofuran-5-yl ethanesulphonate. The arsenic herbicide generally comprises a salt, e.g. the mono- or disodium salt of methane arsonic acid or cacodylic acid. Other herbicides which may be used include 1,2-dimethyl-2,5-diphenyl-pyrazolium ion, ethyl N-benzoyl-N-(3,4-dichlorophenyl)alanine, N-isobutyl-2-oxo-1-imidazolidine-carboxamide, aminotriazole, 2,3-dichloro-1,4-naphthoquinone, 4-amino-3,5,6-trichloropicolinic acid, N,N-dimethyl-2,2-diphenylacetamide, 2,6-dinitro-N,N-dipropyl-4-trifluoromethyl-aniline, N-butyl-N-ethyl-2,6-dinitro-4-trifluoromethylaniline, S,S,S-tributyl phosphorotrithioate, 2-ethoxy-2,3-dihydro-3,3-dimethyl-5-benzofuranyl methylsulphonate, 4-chloro-2-oxobenzothiazolin-3-yl acetic acid, 3-isopropyl-2,1,3-benzothiadiazinon-(4)-2,2-dioxide, 3,5-dibromo-4-hydroxybenzaldehyde, 2,4-dinitrophenyloxime, methyl 2-chloro-3-(4-chlorophenyl)propionate, 2-chloroethyl-trimethylammonium chloride, 4-methylsulphonyloxy-2-butynyl m-chlorocarbanilate, isopropyl 2-(N-benzoyl-3-chloro-4-fluoroanilino)propionate, methyl 2-(N-benzoyl-3-chloro-4-fluoroanilino)propionate, 2-chloro-N-(1,3-dioxolan-2-ylmethyl)-2',6'-dimethylacetanilide, 2-chloro-1-(3-ethoxy-4-nitrophenoxy)-4-trifluoromethylbenzene, methyl 2-(4-[2',4'-dichlorophenoxy]phenoxy)propionate, 1,1,1-trifluoro-2'-methyl-4'-(phenylsulphonyl)methane sulphoanilide, 4-chloro-5-methylamino-2-(3-trifluoromethylphenyl)-3(2H)- pyridazinone, 5-(2-chloro-4-trifluoromethylphenoxy)-2-nitrobenzoic acid, 1-methyl-3-phenyl-5-(3-trifluoromethylphenyl)-4-pyridone, 4-(methylsulphonyl)-2,6-dinitro-N,N-dipropylaniline, 4-(2,4-dichlorophenoxy)-2-methoxy-1-nitrobenzene, N-(1-ethylpropyl)-3,4-dimethyl-2,6-dinitroaniline, 2',4'-dimethyl-5'-(trifluoromethanesulphonamido)acetanilide, dimethyl 2,3,5,6-tetrachloroterephthalate, N-cyclopropylmethyl-2,6-dinitro-N-propyl-4-trifluoromethylaniline, N-(2-chloroethyl)-2,6-dinitro-N-propyl-4-trifluoromethylaniline, N',N'-diethyl-2,6-dinitro-4-trifluoromethyl-m-phenylenediamine, N',N'-dipropyl-2,6-dinitro-4-trifluoromethyl-m-phenylenediamine, N-sec-butyl-4-tert-butyl-2,6-dinitroaniline, 2-(3,4-dichlorophenyl)-4-methyl-1,2,4-oxadiazolidine-3,5-dione, 4-(dipropylamino)-3,5-dinitrobenzenesulphonamide, 1-(3-trifluoromethylphenyl)-3-chloro-4-chloromethyl-2-pyrrolidone, 2-(1-allyloxyaminobutylidine)-5,5-dimethyl-4-methoxycarbonylcyclohexane-1,3-dione, 2-(N-ethoxybutyrimidoyl)-5-(2-ethylthiopropyl)-3-hydroxy-2-cyclohexen-1-one, or 2-(1-(2,5-dimethylphenyl)ethylsulphonyl)pyridine N-oxide.

The compounds of the formula I may also be employed in association with a herbicidal antidote (a substance having the property of improving the safety of a herbicide to a crop), e.g. N,N-diallyl-2,2-dichloroacetamide, 4'-chloro-2-(hydroxyimino)acetanilide, 1,8-naphthalic anhydride, α-(cyanomethoximino)-benzeneacetonitrile or 2,2-dimethyl-3-dichloroacetyloxazolidine. Although the antidote may be applied in admixture with the active compound, it is preferably applied separately, and especially as a treatment for crop seeds. The ratio by weight of herbicide to antidote can vary from 10:1 to 1:4.

The compounds of the formula I are obtained by processes which are known per se. In a first process, the 1,3,4-thiadiazolyloxyphenylureas are obtained by reacting a hydroxyphenylurea of the formula II

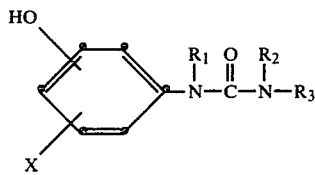
(II)

wherein X, $R_1$, $R_2$ and $R_3$ are as defined for formula I, in an inert organic solvent and in the presence of an acid acceptor, with a 2-halogeno-1,3,4-thiadiazolyl derivative of the formula III

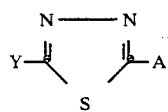
(III)

wherein Y is as defined for formula I and A is halogen or a $C_1$–$C_4$alkylsulfonyl radical.

In another process, the 1,3,4-thiadiazolyloxyphenylureas of the formula I are obtained by reacting a 1,3,4-thiadiazolyloxyaniline of the formula IV

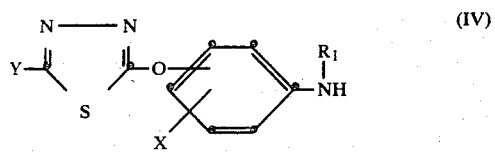
(IV)

wherein X, Y and $R_1$ are as defined for formula I, in an inert organic solvent and in the presence of an acid acceptor, with a carbamoyl halide of the formula V

(V)

wherein Hal is halogen and $R_2$ and $R_3$ are as defined for formula I.

The 1,3,4-thiadiazolyloxyphenylureas of the formula I, wherein $R_1$ is hydrogen, can also be obtained by converting a 1,3,4-thiadiazolyloxyanilide of the formula V, wherein $R_1$ is hydrogen, with phosgene into the 1,3,4-thiadiazolyloxyphenylisocyanate of the formula VI

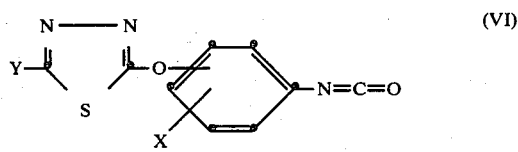
(VI)

wherein X and Y are as defined for formula I, and reacting this compound, in an inert organic solvent, with an amine of the formula VII

(VII)

wherein $R_2$ and $R_3$ are as defined for formula I.

The starting materials of the formulae II and III are known and some are commercially available. The same also applies to the amines of the formula VII and the carbamoyl halide of the formula V.

The aniline of the formula IV is obtained e.g. by condensation of a nitrophenol of the formula VIII

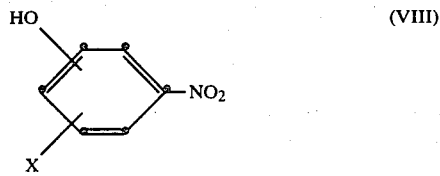
(VIII)

wherein X is as defined for formula I, with the 2-halogeno-1,3,4-thiadiazolyl derivative of the formula III and subsequent reduction of the nitro group to give the amine. If desired, the aniline can additionally be alkylated with a $C_1$–$C_4$alkyl (mono)halide.

The above reactions are conducted in organic solvents which are inert to the reactants, such as ketones, higher boiling alkanols, esters, dimethyl formamide, dimethyl sulfoxide, dioxane etc. It is advantageous to employ watermiscible solvents, as the reaction product can be precipitated by the addition of water.

The reaction temperature is in the range from 0° to 150° C., and usually alternates between room temperature and the boiling point of the reaction mixture. These reactions are usually carried out under normal pressure. For large-scale production, however, it is advisable to use pressure vessels and to apply higher pressures.

The compounds of the formula I have low mammalian toxicity and no precautionary measures are necessary for handling them. They dissolve relatively well in customary organic solvents and are reluctantly soluble in water. They can be readily precipitated by adding water to the reaction solution. It is only possible to formulate them as liquid herbicidal compositions with the aid of special solubilisers and/or dispersants.

The following Examples serve to illustrate the production of the phenylureas of the formula I in more detail. The subsequent tables list further compounds which are obtained in analogous manner. Parts and percentages are by weight, and boiling points are indicated with the temperature and, where they have not been measured under atmospheric pressure, with the indicated pressure in millibars (mbar).

EXAMPLE 1

N-[4-(5'-tert-butyl-1',3',4'-thiadiazolyl-2'-oxy)phenyl]-N',N'-dimethylurea

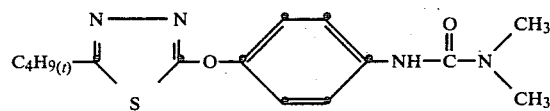

A mixture of 9 g of N-(p-hydroxyphenyl)-N',N'-dimethylurea, 3.3 g of powdered potassium hydroxide and 60 ml of dimethyl sulfoxide is heated for half an hour to 50° C. With stirring and while cooling, 8.9 g of 2-chloro-5-tert-butyl-1,3,4-thiadiazole are added dropwise. After it has been stirred for 2 hours at 70° C., the reaction mixture is poured into ice-water. The precipitated product is filtered with suction, washed with water and dried in vacuo, affording 14 g of the above urea with a melting point of 138°–140° C.

The following compounds were obtained in analogous manner:

| No. | X | Y | Physical data (°C.) |
|---|---|---|---|
| 1.01 | H | C(CH$_3$)$_3$ | m.p. 138–140° |
| 1.02 | H | CF$_3$ | m.p. 138–140° |
| 1.03 | H | CH$_3$ | m.p. 118° |
| 1.04 | H | C$_2$H$_5$ | |
| 1.05 | H | CH(CH$_3$)$_2$ | m.p. 89–91° |
| 1.06 | H | C$_3$H$_{7n}$ | |
| 1.07 | H | SC$_4$H$_{9n}$ | m.p. 73–74° |
| 1.08 | H | CH$_2$CH(CH$_3$)$_2$ | |
| 1.09 | H | CH(C$_2$H$_5$)$_2$ | |
| 1.10 | H | CH(CH$_3$)C$_2$H$_5$ | |
| 1.11 | H | CCl$_3$ | |
| 1.12 | H | cyclopropyl | m.p. 158° |
| 1.13 | H | cyclopropyl-(CH$_2$)- | |
| 1.14 | H | cyclopropyl (fused) | |
| 1.15 | H | cyclohexenyl | |
| 1.16 | H | cyclobutyl | |
| 1.17 | H | SCH$_3$ | |
| 1.18 | H | SCH(CH$_3$)$_2$ | |
| 1.19 | H | SC(CH$_3$)$_3$ | |
| 1.20 | H | SO.CH$_3$ | |
| 1.21 | H | SO$_2$CH$_3$ | |
| 1.22 | H | SO$_2$C$_4$H$_{9n}$ | |
| 1.23 | H | SO$_2$N(CH$_3$)$_2$ | |
| 1.24 | H | phenyl | m.p. 201-2° |
| 1.25 | H | Cl-phenyl | m.p. 213–215° |
| 1.26 | H | Cl,Cl-phenyl | |
| 1.27 | Cl | CF$_3$ | m.p. 185–9° |
| 1.28 | Cl | CH$_3$ | |
| 1.29 | Cl | cyclopropyl | |
| 1.30 | Cl | C(CH$_3$)$_3$ | m.p. 116° |
| 1.31 | Cl | SO$_2$N(CH$_3$)$_2$ | |
| 1.32 | Cl | C(CH$_3$)$_2$CN | |
| 1.33 | Cl | SO$_2$CH$_3$ | |
| 1.34 | Cl | phenyl-H | |
| 1.35 | Cl | phenyl | |
| 1.36 | Cl | CH$_2$CN | |
| 1.37 | Cl | SO$_2$CH(CH$_3$)$_2$ | |
| 1.38 | Cl | SCH$_3$ | |
| 1.39 | Cl | SCH(CH$_3$)$_2$ | |
| 1.40 | CF$_3$ | C(CH$_3$)$_3$ | |

| No. | X | Y | Physical data (°C.) |
|---|---|---|---|
| 2.01 | H | CF$_3$ | m.p. 89–90° |
| 2.02 | H | CH$_3$ | m.p. 103–5° |
| 2.03 | H | cyclopropyl | $n_D^{29}$: 1.5922 |
| 2.04 | H | SO$_2$N(CH$_3$)$_2$ | |
| 2.05 | H | CH(CH$_3$)$_2$ | $n_D^{30}$: 1.5820 |
| 2.06 | H | C(CH$_3$)$_3$ | m.p. 95–96° |

-continued

| No. | | | Physical data |
|---|---|---|---|
| 2.07 | H | Cl-[phenyl]-Cl | m.p. 213–15° |
| 2.08 | H | [phenyl] | m.p. 178–9° |
| 2.09 | H | CH(C$_2$H$_5$)$_2$ | |
| 2.10 | H | SC$_4$H$_{9n}$ | m.p. 78–79° |
| 2.11 | H | CCl$_3$ | |
| 2.12 | H | [cyclohexenyl-H] | |
| 2.13 | H | [cyclopentenyl] | |
| 2.14 | H | SCH$_3$ | |
| 2.15 | H | SC$_3$H$_{7n}$ | |
| 2.16 | H | SO$_2$CH$_3$ | |
| 2.17 | H | SO$_2$C$_4$H$_{9n}$ | |
| 2.18 | H | CH$_2$CF$_3$ | |
| 2.19 | H | CH(CH$_3$)C$_2$H$_5$ | |
| 2.20 | Cl | [cyclopropyl] | |
| 2.21 | Cl | [cyclopropyl]–(CH$_2$)– | |
| 2.22 | Cl | SO$_2$N(CH$_3$)$_2$ | |
| 2.23 | Cl | CH$_3$ | |
| 2.24 | Cl | CH(CH$_3$)$_2$ | |
| 2.25 | Cl | C(CH$_3$)$_3$ | m.p. 91–93° |
| 2.26 | Cl | CH(C$_2$H$_5$)$_2$ | |
| 2.27 | Cl | CH(CH$_3$)C$_2$H$_5$ | |
| 2.28 | Cl | CF$_3$ | |
| 2.29 | Cl | CCl$_3$ | |
| 2.30 | Cl | CH$_2$CN | |
| 2.31 | Cl | C(CH$_3$)$_2$CN | |
| 2.32 | Cl | SCH$_3$ | |
| 2.33 | Cl | SC$_2$H$_5$ | |
| 2.34 | Cl | SCH(CH$_3$)$_3$ | |
| 2.35 | Cl | SC$_4$H$_{9n}$ | |
| 2.36 | Cl | SO$_2$C$_3$H$_{7n}$ | |
| 2.37 | Cl | SO$_2$C(CH$_3$)$_3$ | |
| 2.38 | Cl | SOCH$_3$ | |
| 2.39 | CF$_3$ | C(CH$_3$)$_3$ | |

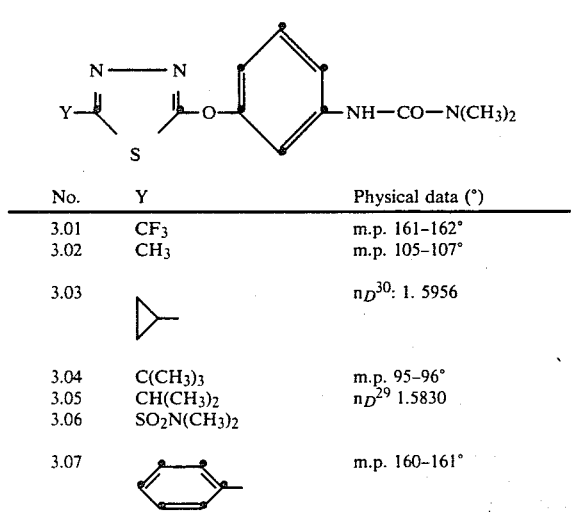

| No. | Y | Physical data (°) |
|---|---|---|
| 3.01 | CF$_3$ | m.p. 161–162° |
| 3.02 | CH$_3$ | m.p. 105–107° |
| 3.03 | [cyclopropyl] | n$_D^{30}$: 1.5956 |
| 3.04 | C(CH$_3$)$_3$ | m.p. 95–96° |
| 3.05 | CH(CH$_3$)$_2$ | n$_D^{29}$ 1.5830 |
| 3.06 | SO$_2$N(CH$_3$)$_2$ | |
| 3.07 | [phenyl] | m.p. 160–161° |
| 3.08 | Cl–[phenyl] | |
| 3.09 | SC$_4$H$_{9n}$ | m.p. 95–96° |
| 3.10 | CH(C$_2$H$_5$)$_2$ | |
| 3.11 | CH(CH$_2$)C$_2$H$_5$ | |
| 3.12 | CCl$_3$ | |
| 3.13 | CH(CH$_3$)CN | |
| 3.14 | SCH$_3$ | |
| 3.15 | SC(CH$_3$)$_3$ | |
| 3.16 | SOCH$_3$ | |
| 3.17 | SO$_2$CH$_3$ | |
| 3.18 | SO$_2$C$_3$H$_{7n}$ | |
| 3.19 | SO$_2$C(CH$_3$)$_3$ | |
| 3.20 | SO$_2$CH(CH$_3$)C$_2$H$_5$ | |
| 3.21 | CH$_2$OCH$_3$ | |

Structure:
Y–C(=N–N=C)–S–O–[phenyl]–NH–CO–N(CH$_3$)(OCH$_3$)

| No. | Y | Physical data (°C.) |
|---|---|---|
| 4.01 | CF$_3$ | m.p. 118–119° |
| 4.02 | CH$_3$ | m.p. 120–124° |
| 4.03 | [cyclopropyl] | n$_D^{30}$: 1.5830 |
| 4.04 | [cyclopropyl]–(CH$_2$)– | |
| 4.05 | [cyclohexenyl-H] | |
| 4.06 | C(CH$_3$)$_3$ | m.p. 124–6° |
| 4.07 | CH(CH$_3$)$_2$ | n$_D^{30}$: 1.5800 |
| 4.08 | SO$_2$N(CH$_3$)$_2$ | |
| 4.09 | [phenyl] | m.p. 108–6° |
| 4.10 | [phenyl-CH$_3$] | m.p. 138–9° |
| 4.11 | CH$_2$OCH$_3$ | |
| 4.12 | CH(C$_2$H$_5$)CN | |
| 4.13 | SC$_4$H$_{9n}$ | m.p. 98–99° |
| 4.14 | SCH(CH$_3$)$_2$ | |
| 4.15 | SOC$_4$H$_{9n}$ | |
| 4.16 | SOC(CH$_3$)$_3$ | |
| 4.17 | SO$_2$CH$_3$ | |
| 4.18 | SO$_2$CH(CH$_3$)$_2$ | |
| 4.19 | SO$_2$CH(CH$_3$)C$_2$H$_5$ | |
| 4.20 | CCl$_3$ | |

The active ingredients (compounds) of the formula I are stable compounds which are soluble in conventional organic solvents, such as alcohols, ethers, ketones, dimethyl formamide, dimethyl sulfoxide etc.

The compositions of the present invention are obtained in known manner by intimately mixing and grinding active ingredients of the general formula I with suitable carriers and/or adjuvants, with or without the addition of antifoams, wetting agents, dispersants and/or solvents which are inert to the active ingredients. The active ingredients can be processed to the following formulations:

solid formulations: dusts, tracking powders, granules (coated granules, impregnated granules and homogeneous granules); active ingredient concentrates which are dispersible in water: wettable powders, pastes, emulsions, emulsion concentrates;

liquid formulations: solutions.

The concentrations of active ingredient in the compositions of this invention are between 1 and 80 percent by weight. As circumstances may require, the active ingredients can also be applied in low concentrations of about 0.05 to 1 percent by weight.

The compositions of the present invention can be mixed with other biocidal compounds or compositions. Thus in addition to containing the compounds of the general formula I, the compositions of the invention can also contain e.g. insecticides, fungicides, bactericides, fungistatic agents, bacteriostatic agents, nematocides or further herbicides, in order to broaden the activity spectrum.

The following Examples will serve to illustrate in more detail the preparation of formulations containing the compounds of the invention. Throughout, parts and percentages are by weight.

Wettable Powders: The following constituents are used to formulate (a) a 70% and (b) a 10% wettable powder:

(a)
70 parts of an active ingredient of the formula I,
5 parts of sodium dibutylnaphthalenesulfate,
3 parts of naphthalenesulfonic acid/phenolsulfonic acid/formaldehyde condensate (3:2:1),
10 parts of kaolin,
12 parts of Champagne chalk;

(b)
10 parts of active ingredient,
3 parts of a mixture of the sodium salts of saturated fatty alcohol sulfates,
5 parts of naphthalenesulfonic acid/formaldehyde condensate,
82 parts of kaolin.

The respective active ingredient is applied to the corresponding carriers (kaolin and chalk) and then these are mixed and ground, to yield wettable powders of excellent wettability and suspension power. By diluting these wettable powders with water it is possible to obtain suspensions containing 0.1 to 8% of actibe ingredient. These suspensions are suitable for controlling weeds in crops of cultivated plants.

Paste: The following substances are used to formulate a 45% paste:
45 parts of active ingredient of the formula I,
5 parts of sodium aluminium silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active ingredient is intimately mixed with the additives in appropriate devices and ground. By diluting the resultant paste with water, it is possible to prepare suspensions of any desired concentration.

Emulsifiable Concentrate: The following ingredients are mixed to formulate a 25% emulsifiable concentrate:
25 parts of an active ingredient of the formula I,
10 parts of a mixture of nonylphenolpolyoxyethylene or calcium dodecylbenzenesulfonate,
10 parts of cyclohexanone,
55 parts of xylene.

This concentrate can be diluted with water to give emulsions in suitable concentrations of e.g. 0.1%. Such emulsions are suitable for controlling weeds in crops of cultivated plants.

The following biological tests were carried out to establish the usefulness of the compounds of the formula I as pre-emergence and post-emergence herbicides and their superiority to known compounds of similar structure.

Pre-emergence herbicidal action (inhibition of germination):

In a greenhouse, immediately after sowing the test plants in seed dishes, the surface of the soil is treated with an aqueous dispersion of the active ingredients, obtained from a 25% emulsifiable concentrate or from a 25% wettable powder with active ingredients which, on account on their insufficient solubility, cannot be formulated to emulsifiable concentrates. Four different concentration series were used, corresponding to 4, 2, 1 and 0.5 kg of active ingredient per hectare respectively. The seed dishes are kept in the greenhouse at 22°–25° C. and 50–70% relative humidity. The test is evaluated 3 weeks later in accordance with the following rating:

1 = plants have not germinated or are totally withered
2–3 = very strong action
4–6 = average action
7–8 = slight action
9 = no action (as untreated control)

The following test plants were used:

| | |
|---|---|
| *hordeum* (barley) | *setatia italica* |
| *triticum* (wheat) | *echinochloa crus galli* |
| *zea* (maize) | *beta vulgaris* |
| *sorghum hybritum* (millet) | *sida spinosa* |
| *oryza* (rice) | *sesbania exaltata* |
| *glycine* (soya) | *amaranthus retroflexus* |
| *gossypium* (cotton) | *sinapis alba* |
| *avena fatua* | *ipomoea purpurea* |
| *lolium perenne* | *galium aparine* |
| *alopecuruc myosuroides* | *pastinaca sativa* |
| *bromus tectorum* | *rumex sp.* |
| *cyperus exculentus* | *chrysanthemum leucum* |
| *rottboelia exaltata* | *abutilon sp.* |
| *digitaria sanguinalis* | *solanum nigrum* |

At rates of application of 1 and 2 kg/ha, the tested compounds of the formula I were most effective against the broad-leafed and also against most of the grass-like weeds, whereas no or only insignificant damage was caused to cultivated plants such as maize and to some extent also wheat, millet, rice, soya and cotton.

Post-emergence herbicidal action (Contact herbicide):

A large number of weeds and cultivated plants, both mono- and dicotyledonous, are sprayed post-emergence in the 4- to 6-leaf stage with an aqueous active ingredient dispersion in rates of 0.5, 1, 2 and 4 kg of active ingredient per hectare and kept at 24°–26° C. and 45–60% relative humidity. The test was evaluated at least 15 days after treatment in accordance with the same rating as employed in the preemergence test.

In this test too the tested compounds were most effective against monocotyledonous and most grass-like weeds at rates of application of 1 and 2 kg/ha, whilst maize, barley, millet and rice, as well as cotton and soya, were not damaged or were only damaged at higher rates of application.

Growth inhibition in grasses

Seeds of the grasses Lolium perenne, Poa pratensis, Festuca ovina, and Dactylis glomerata were sown in plastic dishes filled with an earth/turf/sand mixture (6:3:1) and watered normally. The emergent grasses were cut back weekly to a height of 4 cm above the soil and 40 days after sowing and 1 day after the last cut were sprayed with aqueous spray mixtures of an active ingredient of the formula I. The amount of active ingredient corresponded to a rate of application of 0.5 and 2.5 kg of active ingredient per hectare. The growth of the grasses was evaluated 10 and 21 days after application. Compared with the control, the tested compounds effected an average growth inhibition of 20% at a rate of application of 2.5 kg/ha.

What is claimed is:

1. A 1,3,4-thiadiazolyloxyphenylurea of the formula wherein

X is hydrogen, halogen or trifluoromethyl,

Y is hydrogen, $C_1$–$C_6$ alkyl optionally substituted by halogen or cyano, $C_3$–$C_6$ cycloalkyl, cyclopropylmethyl, phenyl optionally substituted by chlorine or $C_1$–$C_4$ alkyl, $C_1$–$C_4$ alkylthio, $C_1$–$C_4$ alkoxy, $C_1$–$C_4$ alkylsulfinyl, $C_1$–$C_4$ alkylsulfonyl, sulfamoyl or dimethylsulfamoyl, and $R_3$ is methyl or methoxy.

2. A 1,3,4-thiadiazolyloxyphenylurea according to claim 1 of the formula

3. A 1,3,4-thiadiazolyloxyphenylurea according to claim 1 of the formula

4. A 1,3,4-thiadiazolyloxyphenylurea according to claim 2 of the formula

5. A 1,3,4-thiadiazolyloxyphenylurea according to claim 3 of the formula

6. A 1,3,4-thiadiazolyloxyphenylurea according to claim 1 of the formula I, wherein X is hydrogen, chlorine or trifluoromethyl, and Y is trifluoromethyl, isopropyl, isobutyl, sec-butyl, tert-butyl, isoamyl, cyclopropyl, cyclopropylmethyl, methoxymethyl, and 1-cyanopropyl, methylsulfonyl, isopropylsulfonyl or dimethylsulfamoyl.

7. N-[4-(2'-Trifluoromethyl-1',3',4'-thiadiazolyl-5'-oxy)phenyl]-N',N'-dimethylurea according to claim 6.

8. N-[3-(2'-Trifluoromethyl-1',3',4'-thiadiazolyl-5'-oxy)phenyl]-N',N'-dimethylurea according to claim 6.

9. N-[3-Chloro-4-(2'-trifluoromethyl-1',3',4'-thiadiazolyl-5'-oxy)phenyl]-N',N'-dimethylurea according to claim 6.

10. N-[4-(2'-Trifluoromethyl-1',3',4'-thiadiazolyl-5'-oxy)phenyl]-N'-methyl-N'-methoxyurea according to claim 6.

11. N-[3-(2'-Trifluoromethyl-1',3',4'-thiadiazolyl-5'-oxy)phenyl]-N'-methyl-N'-methoxyurea according to claim 6.

12. N-[4-(2'-tert-Butyl-1',3',4'-thiadiazolyl-5'-oxy)phenyl]-N',N'-dimethylurea according to claim 6.

13. N-[3-Chloro-4-(2'-tert-butyl-1',3',4'-thiadiazolyl-5'-oxy)phenyl]-N',N'-dimethylurea according to claim 6.

14. N-[3-Chloro-4-(2'-tert-butyl-1',3',4'-thiadiazolyl-5'-oxy)phenyl]-N'-methyl-N'-methoxyurea according to claim 6.

15. N-[3-(2'-tert-Butyl-1',3',4'-thiadiazolyl-5'-oxy)phenyl]-N',N'-dimethylurea according to claim 6.

16. N-[3-(2'-tert-Butyl-1',3',4'-thiadiazolyl-5'-oxy)phenyl]-N'-methyl-N'-methoxyurea according to claim 6.

17. N-[4-(2'-Isopropyl-1',3',4'-thiadiazolyl-5'-oxy)phenyl]-N',N'-dimethylurea according to claim 6.

18. N-[4-(2'-Isopropyl-1',3',4'-thiadiazolyl-5'-oxy)phenyl]-N'-methyl-N'-methoxyurea according to claim 6.

19. N-[3-(2'-Isopropyl-1',3',4'-thiadiazolyl-5'-oxy)phenyl]-N',N'-dimethylurea according to claim 6.

20. N-[3-(2'-Isopropyl-1',3',4'-thiadiazolyl-5'-oxy)phenyl]-N'-methyl-N'-methoxyurea according to claim 6.

21. A herbicidal composition which contains, as active ingredient, a herbicidally effective amount of a 1,3,4-thiadiazolyloxyphenyl according to claim 1, together with a suitable carrier.

22. A method of selectively controlling weeds in crops of cultivated plants, which comprises applying to said crops a herbicidally effective amount of a 1,3,4-thiadiazolyloxyphenylurea according to claim 1.

* * * * *